United States Patent
Omi (10) Patent No.: US 11,000,253 B2
(45) Date of Patent: May 11, 2021

(54) IMAGE PROCESSING APPARATUS, RADIATION IMAGING APPARATUS, IMAGE PROCESSING METHOD, AND STORAGE MEDIUM

(71) Applicant: CANON KABUSHIKI KAISHA, Tokyo (JP)

(72) Inventor: Hiroyuki Omi, Kamakura (JP)

(73) Assignee: CANON KABUSHIKI KAISHA, Tokyo (JP)

(*) Notice: Subject to any disclaimer, the term of this patent is extended or adjusted under 35 U.S.C. 154(b) by 124 days.

(21) Appl. No.: 16/255,097

(22) Filed: Jan. 23, 2019

(65) Prior Publication Data

US 2019/0231293 A1  Aug. 1, 2019

(30) Foreign Application Priority Data

Jan. 31, 2018 (JP) .............................. JP2018-015504

(51) Int. Cl.
*G06K 9/00* (2006.01)
*A61B 6/00* (2006.01)
(Continued)

(52) U.S. Cl.
CPC .............. *A61B 6/5282* (2013.01); *A61B 6/00* (2013.01); *A61B 6/03* (2013.01); *G01V 5/0025* (2013.01);
(Continued)

(58) Field of Classification Search
CPC ..... A61B 6/032; A61B 6/5264; A61B 6/5282; G06T 2207/10116; G06T 5/002;
(Continued)

(56) References Cited

U.S. PATENT DOCUMENTS

| 7,912,180 | B2* | 3/2011 | Zou ........................ A61B 6/032 378/7 |
| 2014/0334702 | A1* | 11/2014 | El Fakhri .............. G06T 11/005 382/131 |
| 2017/0055932 | A1* | 3/2017 | Lee ......................... A61B 6/027 |
| 2017/0055933 | A1* | 3/2017 | Kawamura ............. G06T 5/002 |

FOREIGN PATENT DOCUMENTS

JP    5388680 B    1/2014

OTHER PUBLICATIONS

Rührnschopf, Ernst-Peter, and Klaus Klingenbeck. "A general framework and review of scatter correction methods in x-ray cone-beam computerized tomography. Part 1: Scatter compensation approaches." Medical physics 38.7 (2011): 4296-4311. (Year: 2011).*

(Continued)

*Primary Examiner* — Li Liu
(74) *Attorney, Agent, or Firm* — Carter, DeLuca & Farrell LLP (57) ABSTRACT

An image processing apparatus for processing a moving image obtained by irradiating an object with radiation, includes: an obtaining unit configured to obtain an amount of change between frames in the moving image; an estimating unit configured to estimate, based on the amount of change, a scattered ray component of the radiation scattered by the object in a frame of the moving image; and a scattered ray reducing unit configured to generate an image by subtracting the scattered ray component from the frame of the moving image.

21 Claims, 5 Drawing Sheets

(51) Int. Cl.
*G01V 5/00* (2006.01)
*A61B 6/03* (2006.01)
*H04N 5/235* (2006.01)
*H04N 5/232* (2006.01)
*G06F 9/30* (2018.01)
*H04N 5/32* (2006.01)

(52) U.S. Cl.
CPC ....... *G06F 9/30003* (2013.01); *H04N 5/2354* (2013.01); *H04N 5/23229* (2013.01); *H04N 5/32* (2013.01)

(58) Field of Classification Search
CPC ................... G06T 5/50; G06T 11/005; G06T 2207/10016; G06T 2207/20224; G06T 7/20; G06T 7/254
See application file for complete search history.

(56) References Cited

OTHER PUBLICATIONS

Rührnschopf and, Ernst-Peter, and Klaus Klingenbeck. "A general framework and review of scatter correction methods in cone beam CT. Part 2: scatter estimation approaches." Medical physics 38.9 (2011): 5186-5199. (Year: 2011).*
Hutton, Brian F., Irene Buvat, and Freek J. Beekman. "Review and current status of SPECT scatter correction." Physics in Medicine & Biology 56.14 (2011): R85. (Year: 2011).*
Trotter, Dinko E. Gonzalez, et al. "Thickness-dependent scatter correction algorithm for digital mammography." Medical Imaging 2002: Physics of Medical Imaging. vol. 4682. International Society for Optics and Photonics, 2002. (Year: 2002).*

* cited by examiner

IMAGE PROCESSING APPARATUS, RADIATION IMAGING APPARATUS, IMAGE PROCESSING METHOD, AND STORAGE MEDIUM

BACKGROUND OF THE INVENTION

Field of the Invention

The present invention relates to an image processing apparatus, a radiation imaging apparatus, an image processing method, and a storage medium.

Description of the Related Art

In medical sites, diagnoses and treatments based on imaging using radiation are frequently performed, and a digital image diagnosis based on a radiation image captured by using a flat panel sensor (sensor) is in widespread use.

In imaging using radiation, two components, that is, primary radiation straightly transmitted through a human body and a scattered ray scattered by the human body structure are generated. The scattered ray is superimposed on an image as a low-frequency component of the structure of an object and hence decreases the contrast of the whole image, and this may deteriorate the diagnostic performance.

A technique which reduces this scattered ray by image processing without using any grid has been developed. When estimating the scattered ray by a method of iterative approximation as the technique of reducing the scattered ray by image processing, the scattered ray reducing process requires a long time.

Japanese Patent No. 5388680 discloses a technique using the scattered ray estimation result of a preceding frame, as a technique which accelerates scattered ray estimation.

This technique of Japanese Patent No. 5388680 uses the scattered ray estimation result of a preceding frame as the initial value of scattered ray estimation in the next frame, and is based on the assumption that an object is not moving between adjacent frames. When performing, for example, high-speed moving image capturing such as CT, it can be assumed that objects in adjacent frames are the same.

Unfortunately, moving image capturing for positioning of still image capturing, moving image capturing for dynamic analysis, and tomosynthesis imaging are not as high-speed moving image capturing as CT, and it cannot be assumed that objects in adjacent frames are the same. Therefore, the convergence decreases in iterative calculations of iterative approximation, and a case in which the influence of the scattered ray cannot be reduced may occur.

The present invention has been made in consideration of the problem of the related art, and provides an image processing technique capable of reducing the influence of the scattered ray and obtaining an image having higher image quality even in moving image capturing using no grid.

SUMMARY OF THE INVENTION

According to one aspect of the present invention, there is provided an image processing apparatus for processing a moving image obtained by irradiating an object with radiation, comprising: an obtaining unit configured to obtain an amount of change between frames in the moving image; an estimating unit configured to estimate, based on the amount of change, a scattered ray component of the radiation scattered by the object in a frame of the moving image; and a scattered ray reducing unit configured to generate an image by subtracting the scattered ray component from the frame of the moving image.

The present invention can reduce the influence of the scattered ray and obtain an image having higher image quality even in moving image capturing using no grid.

Further features of the present invention will become apparent from the following description of exemplary embodiments (with reference to the attached drawings).

DESCRIPTION OF THE EMBODIMENTS

Embodiments of the present invention will exemplarily be explained in detail below with reference to the accompanying drawings. However, the constituent elements described in the embodiments are merely examples, and the technical scope of the present invention is determined by the scope of claims and is not limited by the following individual embodiments.

First Embodiment

Figure 1:
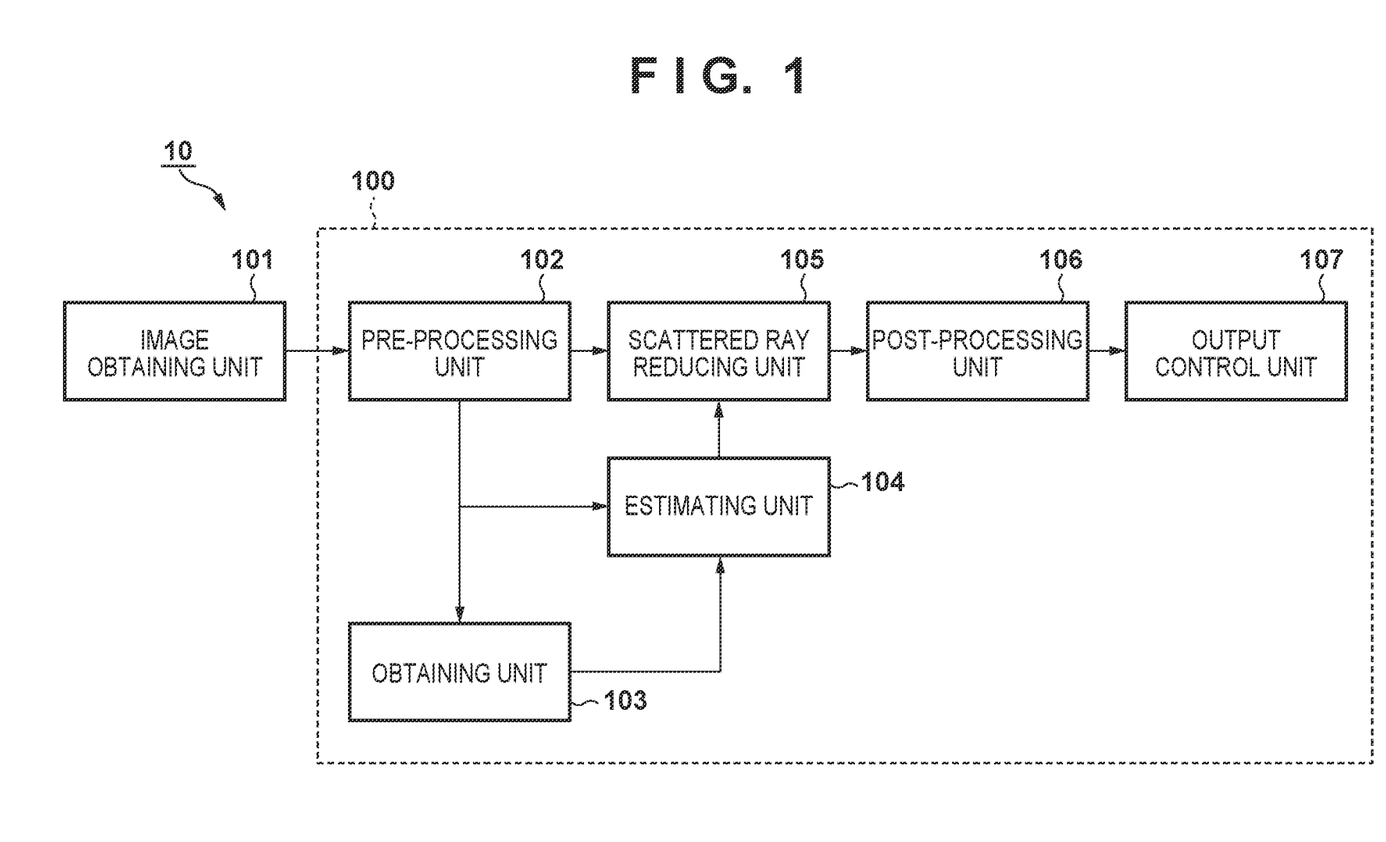
FIG. 1 is a view showing the functional configurations of a radiation imaging apparatus and an image processing apparatus of an embodiment.

FIG. 1 is a view showing an outline of the functional configurations of a radiation imaging apparatus 10 and an image processing apparatus 100 according to an embodiment of the present invention. As functional elements, the radiation imaging apparatus 10 includes, for example, an image obtaining unit 101 and the image processing apparatus 100. Referring to FIG. 1, the image processing apparatus 100 can process a moving image obtained by irradiating an object with radiation, and includes, as functional elements, a pre-processing unit 102, an obtaining unit 103 (to be also referred to as "an amount of change obtaining unit" hereinafter), an estimating unit 104 (to be also referred to as "a scattered ray estimating unit" hereinafter), a scattered ray reducing unit 105, a post-processing unit 106, and an output control unit 107. Note that the output control unit 107 may also be an external control apparatus 201 of the image processing apparatus 100.

In the radiation imaging apparatus 10, the image obtaining unit 101 is, for example, a functional element equivalent to a radiation sensor (to be also simply referred to as "a sensor" hereinafter) of the radiation imaging apparatus 10. The image obtaining unit 101 receives radiation transmitted through an object, and outputs an image of the input radiation. An image to be formed by the image obtaining unit 101 will be called "a raw image" hereinafter, and the raw image is input to the pre-processing unit 102 of the image processing apparatus 100.

The pre-processing unit 102 of the image processing apparatus 100 receives the raw image, generates an image (to be referred to as "a pre-processed image" hereinafter) by performing pre-processing on the raw image, and outputs the generated image.

The obtaining unit 103 (an amount of change obtaining unit) estimates (obtains) the amount of change between frames in a moving image. The amount of change between frames (to be also referred to as "the amount of motion" hereinafter) includes, for example, the amount of motion based on the motion of an object or the motion of a sensor between images (between frames). The obtaining unit 103 (an amount of change obtaining unit) estimates the amount of motion based on the motion of an object or a sensor in a moving image. The amount of change obtaining unit 103 receives a plurality of pre-processed images, and obtains the amount of change (the amount of motion) between images (between frames). That is, the amount of change obtaining unit 103 obtains the difference between a frame (k) as a processing target and a preceding frame (k-1) of the frame (k), as the amount of change (the amount of motion).

When an object is irradiated with radiation, a part of the radiation is scattered by individual portions of the object and generates a scattered ray component. Therefore, the radiation transmitted through the object contains this scattered ray component in addition to a primary radiation component (to be also referred to as "a primary component of radiation", "a straight component of radiation", or "a primary X-ray component") straightly transmitted through the object.

In a frame of the moving image, the estimating unit 104 (a scattered ray estimating unit) estimates, based on the amount of change, the scattered ray component of the radiation scattered in the object. The scattered ray estimating unit 104 can also estimate, based on the amount of change, the scattered ray component of the radiation scattered by the object, and the primary component of the radiation transmitted through the object and directly incident on the sensor, in each frame of the moving image. The scattered ray estimating unit 104 receives the amount of change and the pre-processed image, estimates the scattered ray, and generates and outputs a scattered-ray image. When the obtaining unit 103 (an amount of change obtaining unit) obtains, for example, the amount of motion based on the motion of the object or the motion of the sensor between images (between frames), as the amount of change between frames of the moving image, the estimating unit 104 (a scattered ray estimating unit) estimates the scattered ray component of the radiation scattered by the object, in a frame of the moving image.

The scattered ray reducing unit 105 generates an image (scattered ray reduced image) by subtracting the scattered ray component from a frame in the moving image. That is, the scattered ray reducing unit 105 receives the pre-processed image and the scattered-ray image, generates a scattered ray reduced image by reducing (subtracting) the scattered ray component from the pre-processed image, and outputs the generated image.

The post-processing unit 106 receives the scattered ray reduced image, generates an image (to be referred to as "a post-processed image" hereinafter) by performing frequency processing and gradation processing, and outputs the generated image.

The output control unit 107 performs output control for causing a display unit (monitor) to display the image (the post-processed image (radiation image)) processed by the post-processing unit 106 of the image processing apparatus 100, saving the image in a memory such as a hard disk, or outputting the image to an external apparatus (system) such as a PACS.

Figure 2:
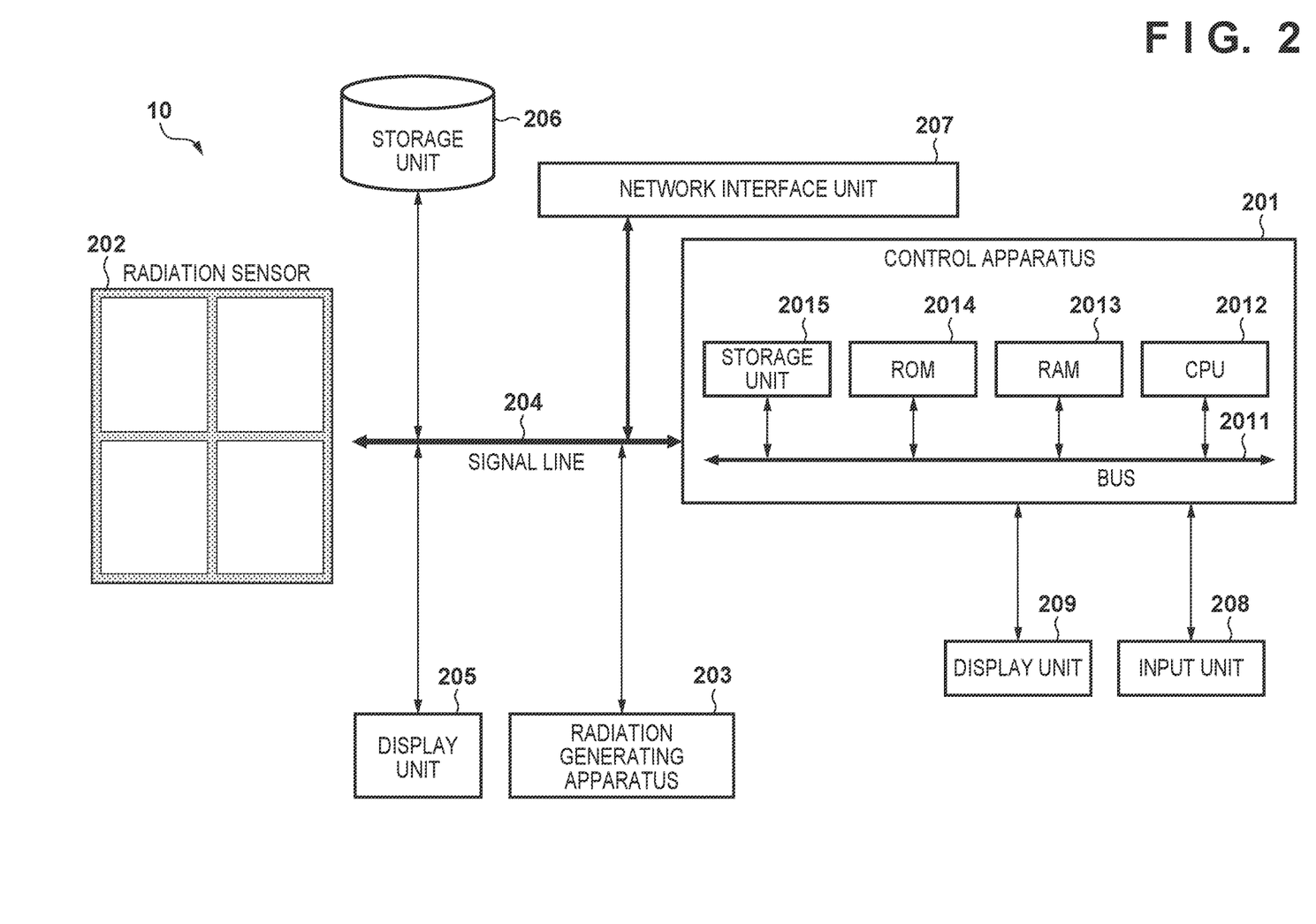
FIG. 2 is a view showing the hardware configurations of the radiation imaging apparatus and a control apparatus.

FIG. 2 is a view showing the hardware configurations of the radiation imaging apparatus 10 and the control apparatus 201 (a console) for controlling the operation of the radiation imaging apparatus 10. Referring to FIG. 2, a signal line 204 is a signal line capable of exchanging signals complying with the gigabit Ethernet (Ethernet is a registered trademark) standards, and the control apparatus 201, a radiation sensor 202, and a radiation generating apparatus 203 are connected via the signal line 204 so that they can communicate with each other. The radiation sensor 202 is equivalent to the image obtaining unit 101 explained with reference to FIG. 1, and outputs a raw image by imaging the input radiation. In long-size imaging using a plurality of radiation sensors as an arrangement of the radiation sensor 202, a plurality of radiation sensors are connected to the signal line 204.

Note that the signal line shown in FIG. 2 is not limited to a signal line complying with the gigabit Ethernet (Ethernet is a registered trademark) standards, and it is also possible to use, for example, a CAN (Controller Area Network), an optical fiber, or the like as the signal line. The signal line 204 is connected to a display unit 205 for displaying a post-processed image (radiation image) output from the output control unit 107, a storage unit 206 for storing the post-processed image, and a network interface unit 207 for outputting the post-processed image to an external apparatus (system) such as a PACS.

As the hardware configuration of the control apparatus 201, for example, a CPU (Central Processing Unit) 2012, a RAM (Random Access Memory) 2013, a ROM (Read Only Memory) 2014, and a storage unit 2015 are connected via a bus 2011.

The control apparatus 201 is connected to an input unit 208 via a connecting portion complying with the USB (Universal Serial Bus) or the PS/2 standards, and connected to a display unit 209 via a connecting portion such as a VGA or DVI terminal. The control apparatus 201 can transmit control commands to the radiation sensor 202, the display unit 205, and the like connected via the signal line 204.

Software modules for executing the contents of processing corresponding to individual imaging modes are stored in the storage unit 2015 of the control apparatus 201. A software module corresponding to an imaging mode designated by a designating unit (not shown) is read out to the RAM 2013, and processing is executed under the control of the CPU (Central Processing Unit) 2012. The CPU (Central Processing Unit) 2012 can control the execution of a software module as each unit in the functional configuration of the image processing apparatus 100 shown in FIG. 1.

That is, the units from the pre-processing unit 102 to the post-processing unit 106 and the output control unit 107 are stored as software modules in the storage unit 2015, and the CPU 2012 can implement the function of each of these units from the pre-processing unit 102 to the output control unit 107 by executing the corresponding software module. Note that the function of each unit of the image processing apparatus 100 may also be installed as a dedicated image processing board, instead of a software module, in the control apparatus 201.

Each of the display unit 205 and the storage unit 206 connected to the control apparatus 201 via the signal line 204, or the display unit 209 connected to the control apparatus 201 via the connecting portion such as a VGA terminal or a DVI terminal, functions as an image output unit. The output control unit 107 shown in FIG. 1 controls image display and storage of image data in the image output units (the display units 205 and 209 and the storage unit 206). That is, the output control unit 107 controls output of the post-processed image (radiation image) generated by the image processing apparatus 100, so as to display the post-processed image (radiation image) on the display unit 205 or 209, or store the post-processed image in the storage unit 206 or 2015.

Practical operations of the functional elements (the units from the pre-processing unit 102 to the output control unit 107) shown in FIG. 1 as the features of this embodiment in the radiation imaging apparatus 10, the control apparatus 201, and the image processing apparatus 100 having the configurations as described above will be explained below.

Figure 3:
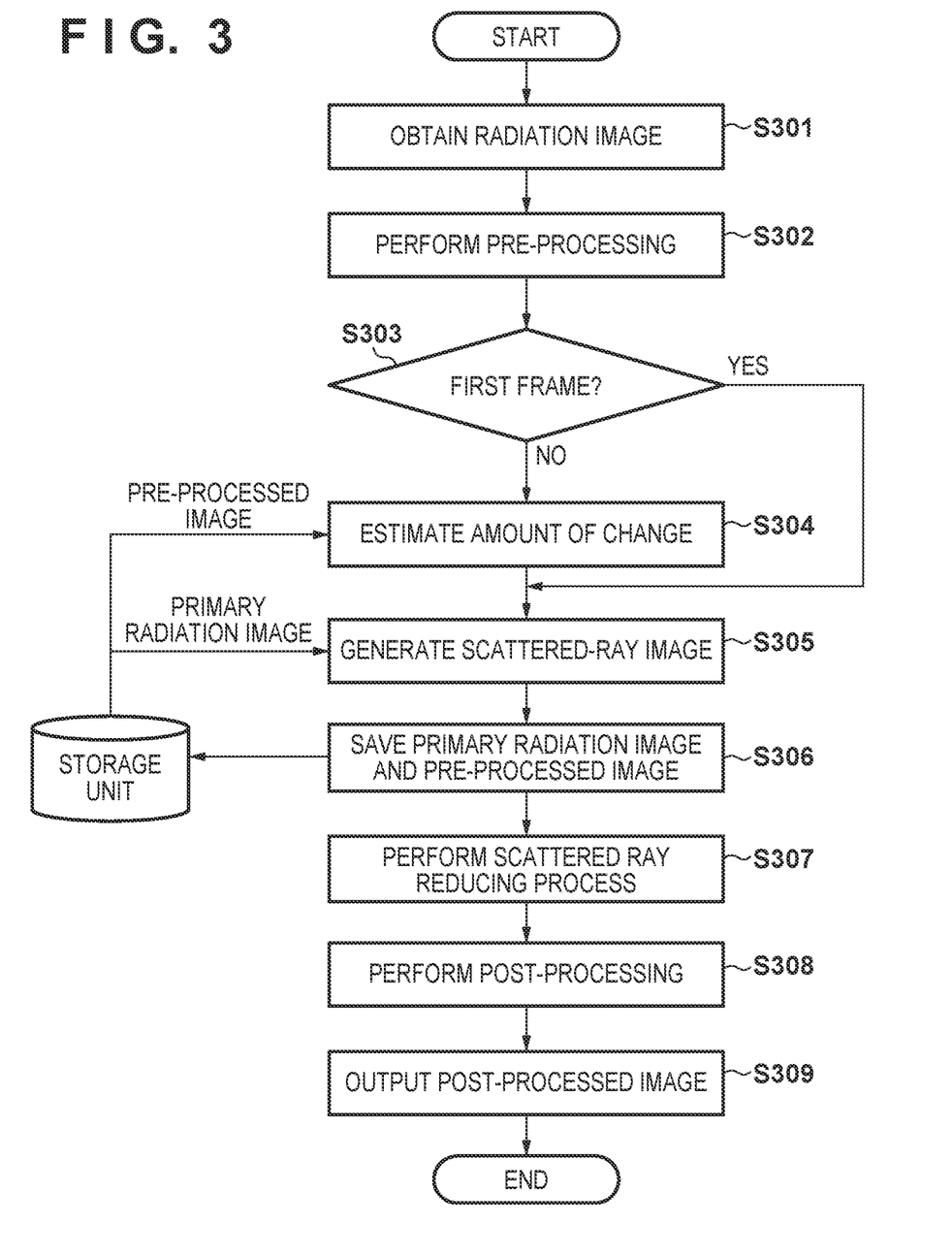
FIG. 3 is a flowchart for explaining the procedure of image processing according to the embodiment.

FIG. 3 is a flowchart for explaining the procedure of image processing according to the embodiment. First, processing of the first frame of a moving image will be explained.

(Processing of First Frame of Moving Image)

In step S301, the image obtaining unit 101 obtains an image by the radiation sensor 202, and generates a raw image by performing offset correction (dark current correction). For example, this offset correction can be performed by obtaining image data of an object not irradiated with radiation as a correction image before a radiation image of the object is obtained, and subtracting the correction image from a radiation image obtained by imaging the object with irradiation. Alternatively, the offset correction can be performed by alternately obtaining a radiation image by irradiating an object with radiation and obtaining image data (a correction image) of the object without irradiation, and subtracting the correction image from the radiation image.

In step S302, the pre-processing unit 102 performs pre-processing on the raw image, thereby generating a pre-processed image. The pre-processing is, for example, a process of correcting the sensor characteristics, and the pre-processing unit 102 performs gain correction, defect correction, and the like, thereby holding the correlation to peripheral pixels. Note that this pre-processing in step S302 may also be skipped.

In step S303, the CPU (Central Processing Unit) 2012 determines whether a frame to be processed is the first frame of moving image capturing. If the frame to be processed is not the first frame (NO in step S303), the CPU (Central Processing Unit) 2012 advances the process to step S304. If the frame to be processed is the first frame (YES in step S303), the CPU (Central Processing Unit) 2012 advances the process to step S305.

In step S305, the scattered ray estimating unit 104 estimates a scattered ray component by performing a scattered ray estimating process on the pre-processed image, and generates a scattered ray image. The radiation sensor 202 (a sensor) can measure a pre-processed image M(k), and a primary component P(k) of radiation transmitted through the object and directly incident on the sensor and a scattered ray component S(k) of radiation scattered by the object are combined in the component of the pre-processed image M(k). The primary component P(k) of the radiation is an unscattered radiation transmitted through the object and directly incident on the sensor. k indicates the kth frame of the moving image.

The scattered ray component S(k) of the kth frame can be obtained by the difference between the component of the pre-processed image M(k) and the primary component P(k) of the radiation, and the scattered ray estimating unit 104 can obtain the scattered ray component S(k) of the kth frame by equation (1) below:

$$S(k)=M(k)-P(k) \quad (1)$$

Also, the scattered ray component S(k) can be modeled by adding up the low-frequency component of the scattered ray and the high-frequency component of the scattered ray. When practically showing modeling of the scattered ray component S(k) by a numerical expression, the scattered ray component S(k) can be modeled by equation (2) below:

$$S(k,x,y)=-AP(k,x,y)\log P(k,x,y)*e^{-B(x^2+y^2)}-CP(k,x,y)\log P(k,x,y)*(1-e^{-B(x^2+y^2)}) \quad (2)$$

In equation (2), a coefficient A is a parameter indicating the low-frequency component of attenuated scattered radiation, B is a parameter indicating the spread of the attenuated scattered radiation, and C is a parameter indicating the high-frequency component of the attenuated scattered radiation. In addition, x and y are position information representing the coordinate position.

The problem of estimating the scattered ray can be solved by obtaining the primary component P(k) of the radiation from the component of the pre-processed image M(k) based on equations (1) and (2). However, the component of the pre-processed image M(k) and the primary component P(k) of the radiation cannot analytically be obtained. Therefore, an estimated primary component Pg(k) of the radiation is calculated, and an iterative calculation is performed such that an error E between the component of a pre-processed image Mg(k) estimated based on the primary component Pg(k) and the component of the actual pre-processed image M(k) decreases. Subscript g indicates a value estimated by the calculation.

In the iterative calculation of the primary component of the radiation, the scattered ray estimating unit 104 estimates the component of the image M(k) generated by pre-processing the frame (k) to be processed, based on the estimated primary component Pg(k) of the radiation and the scattered ray component (S(k)). The estimated component of the pre-processed image is Mg(k).

Then, in the iterative calculation of the primary component of the radiation, the scattered ray estimating unit 104 obtains an estimated value of an image component which minimizes the value (error E) based on the difference between the image component of the image (pre-processed image M(k)) generated by pre-processing the frame to be processed, and the estimated pre-processed image component (Mg(k)). The scattered ray estimating unit 104 obtains the primary component of the radiation based on the obtained image component estimated value, and a scattered ray component corresponding to this primary radiation component.

An evaluation expression of the error E can be represented by equation (3) below which squares the absolute value of the difference between the component of the actual pre-processed image M(k) and the component of the pre-processed image Mg(k) estimated by the calculation.

$$E=|M(k)-M_g(k)|^2 \quad (3)$$

The primary component Pg(k) of the radiation is approximated by equation (4) by using the component of the pre-processed image M(k) which minimizes the error evaluation formula of equation (3), and the component of the estimated pre-processed image Mg(k). It is possible to use, for example, maximum-likelihood estimation as a method of iteratively calculating the primary component Pg(k) of the radiation. The scattered ray estimating unit 104 can obtain the primary component of the radiation from the relationship of equation (4) based on the image component estimated value ((Mg(k)) which minimizes the error evaluation formula, and obtain the scattered ray component from the relationship of equation (1) based on the obtained primary radiation component.

The scattered ray estimating unit 104 estimates the primary component (Pg(k)n+1) of radiation when the number of iterations is n+1 (n is an integer equal to 2 or more), from the result of multiplication of the result of division of dividing the image component (the component of the pre-processed image M(k)) of the frame to be processed, by the sum (Pg(k)n+S(k)n) of the primary component and scattered ray component of radiation when the number of iterations is n, and the primary component (Pg(k)n) of the radiation.

More specifically, as indicated by equation (4), the component of the pre-processed image M(k) is divided by the sum of the primary component Pg(k)n and scattered ray component S(k)n of the radiation when the number of iterations is n, and the result of the division is multiplied by the primary component Pg(k)n of the radiation, thereby approximating the primary component Pg(k)n+1 of the radiation in the iterative calculation performed n+1 times.

In equation (4), the primary component Pg(k)n of the radiation in the n-time iterations is a primary radiation component corresponding to the estimated pre-processed image Mg(k) which minimizes the error E of equation (3).

The scattered ray component S(k)n is a scattered ray image calculated by equation (1) based on the primary component Pg(k)n of the radiation in the n-time iterations. In equation (4), n indicates the number of iterations.

$$P_g(k)^{n+1} = \frac{M(k)}{P_g(k)^n + S(k)^n} P_g(k)^n \quad (4)$$

In the maximum-likelihood estimation indicated by equation (4), the coefficient part (equation (5)) of the primary component Pg(k)n of the radiation approaches 1 and converges whenever iteration is performed. That is, the component (the denominator of equation (5) below) of the estimated pre-processed image Mg(k) approaches the component (the numerator of equation (5)) of the actual pre-processed image M(k) and converges. If the approach to 1 is fast, it is possible to reduce the number of iterations, and increase the operation speed of estimation.

$$\frac{M(k)}{P_g(k)^n + S(k)^n} \quad (5)$$

In the scattered ray estimating process for the pre-processed image, the scattered ray estimating unit 104 sets the component of the pre-processed image M(k) as the initial value of the primary component Pg(k) of the radiation in the first frame. The number of iterations can be a preset number, or can be set such that iteration is performed until the error E becomes a predetermined value. The scattered ray estimating unit 104 calculates the primary radiation component Pg(k)n which is close to the true value by iteratively executing the scattered ray estimating process. The scattered ray estimating unit 104 calculates the scattered ray component S(k) based on equation (1) from the component of the actual pre-processed image M(k) and the primary radiation component Pg(k)n, and outputs the calculated scattered ray component S(k).

In step S306, the scattered ray estimating unit 104 stores, in the storage unit 2015, an image (primary radiation image) based on the primary radiation component Pg(k)n calculated in step S305, and the pre-processed image M(k), for processing for the next and subsequent frames.

Then, in step S307, the scattered ray reducing unit 105 performs a scattered ray reducing process. The scattered ray reducing unit 105 generates an image (scattered ray reduced image) by subtracting the scattered ray component corresponding to the primary radiation component obtained by the scattered ray estimating unit 104 from an image component generated by pre-processing a frame to be processed. That is, the scattered ray reducing unit 105 generates the scattered ray reduced image by subtracting the scattered ray component S(k) obtained in step S305 from the pre-processed image (the component of the actual pre-processed image M(k)).

An image like that in a case using a grid can be generated by associating the weight of the subtracting process with the grid ratio of the grid. Since the scattered ray component S(k) contains a large amount of low-frequency components, the scattered ray reduced image from which the scattered ray component S(k) is removed increases the contrast as a whole compared to the pre-processed image.

Subsequently, in step S308, the post-processing unit 106 performs post-processing on the scattered ray reduced image, thereby generating a post-processed image. The post-processing is a process of generating an image optimum for a diagnosis, and the post-processing unit 106 performs frequency processing, gradation processing, and the like on the scattered ray reduced image.

In step S309, the output control unit 107 outputs the post-processed image having undergone the post-processing in step S308 to the image output unit (the display unit 205 or 209, or the storage unit 206). The output control unit 107 performs output control for displaying the post-processed image processed by the post-processing unit 106 on the display unit (monitor), saving the image in a memory such as a hard disk, or outputting the image to an external apparatus (system) such as a PACS.

(Processing of Second and Subsequent Frames of Moving Image)

Next, processing of the second and subsequent frames of the moving image will be explained. Processes in steps S301 and S302 are the same as the processes for the first frame, so an explanation thereof will be omitted.

Then, in determination of step S303, the CPU (Central Processing Unit) 2012 determines whether a frame to be processed is the first frame of moving image capturing. If the frame to be processed is not the first frame (NO in step S303), the CPU (Central Processing Unit) 2012 advances the process to step S304.

In step S304, the amount of change obtaining unit 103 receives a plurality of pre-processed images and estimates (obtains) the amount of change between frames. That is, the amount of change obtaining unit 103 estimates (obtains) the amount of change between frames based on the difference between a pre-processed image of the current frame and a pre-processed image of the preceding frame, as the plurality of pre-processed images.

More specifically, the amount of change obtaining unit 103 obtains an estimated value D(k) of the amount of change between frames as indicated by equation (6), from the component of the pre-processed image M(k) of the current frame (kth frame) and the component of a pre-processed image M(k-1) of the preceding frame ((k-1)th frame) stored in the storage unit 2015.

$$D(k)=M(k)-M(k-1) \quad (6)$$

Figure 4:
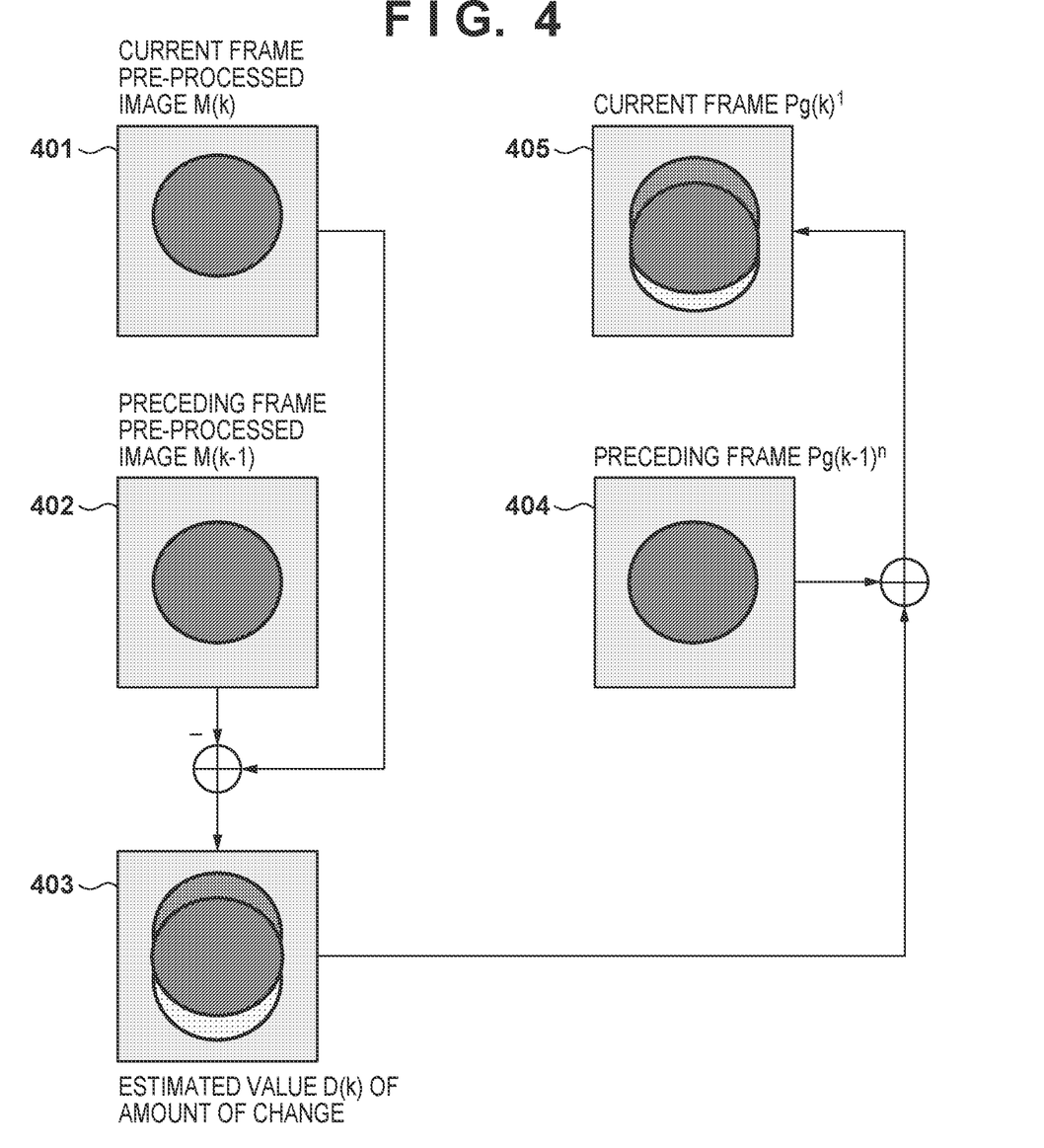
FIG. 4 is a view schematically showing an estimated value of the amount of motion and the initial value of a primary radiation image.

In FIG. 4, an image 401 is the pre-processed image M(k) of the current frame, and an image 402 is the pre-processed image M(k-1) of the preceding frame. An estimated value D(k) 403 of the amount of change is obtained as a motion component by calculating the difference between the pixel values of the two images.

Then, in step S305, the scattered ray estimating unit 104 performs a scattered ray estimating process based on the pre-processed image M(k) of the current frame, the estimated value D(k) of the amount of change, and the image (primary radiation image) stored in the storage unit 2015 and based on the primary component Pg(k-1)n of the radiation in the preceding frame, thereby generating a scattered ray image.

The scattered ray estimating unit 104 estimates the primary component of the radiation by the iterative calculation, and sets, as the initial value of the iterative calculation of the frame (k) to be processed, a value obtained by combining the primary radiation component estimated in the preceding frame (k-1) of the frame (k) and the amount of change (the estimated value D(k) of the amount of change).

That is, in the processing of the second and subsequent frames, the scattered ray estimating unit 104 sets a value taking account of the estimated value D(k) of the amount of change as indicated by equation (7), as the initial value (a value when number of iterations n=1) of the primary component Pg(k) of the radiation. Equation (8) is obtained by substituting, as the initial value, equation (7) taking account of the estimated value D(k) of the amount of change into equation (4). Equation (8) shows a case in which number of iterations n=2. As indicated by equation (8), the estimated value D(k) of the amount of change is reflected on the iterative calculation.

$$P_g(k)^1 = P_g(k-1)^n + D(k) \quad (7)$$

$$P_g(k)^2 = \frac{M(k)}{P_g(k)^1 + S(k)^1} P_g(k)^1 \quad (8)$$

$$= \frac{M(k)}{P_g(k-1)^n + D(k) + S(k)^1}(P_g(k-1)^n + D(k))$$

As in the processing of the first frame, the scattered ray estimating unit 104 performs an iterative calculation so that the error E of equation (3) decreases. In equation (4), the primary component Pg(k)n of the radiation in the n-time iterations is a primary radiation component corresponding to the component of the estimated pre-processed image Mg(k) which minimizes the error E of equation (3), and the scattered ray component S(k)n is a scattered ray component calculated by equation (1) based on the primary component Pg(k)n of the radiation in the n-time iterations. The scattered ray estimating unit 104 calculates the scattered ray component S(k) by equation (1) from the component of the actual pre-processed image M(k) and the primary component Pg(k)n of the radiation, and outputs the calculated scattered ray component S(k) as a scattered ray image.

In FIG. 4, an image 405 is an initial value Pg(k)1 of the primary component Pg(k) of the radiation in the current frame (k), and a value obtained by adding the estimated value D(k) 403 of the amount of change to the primary radiation component Pg(k-1)n (an image 404 in FIG. 4) calculated in the preceding frame (k-1) is set.

The initial value Pg(k)1 of the primary radiation component Pg(k) in the current frame (k) is corrected based on the estimated value D(k) 403 of the amount of change and the primary radiation component Pg(k-1)n calculated in the preceding frame (k-1). This makes it possible to reflect the amount of change (the amount of motion) between frames on the setting of the initial value of the primary radiation component in the current frame (k), and set a more suitable initial value.

The difference between the primary radiation component P(k) in the current frame (k) and the primary radiation component P(k-1) in the preceding frame (k-1) can be approximated by the difference between the component of the pre-processed image M(k) in the current frame (k) and the component of M(k-1) in the preceding frame (k-1). Therefore, a value close to the primary radiation component Pg(k) in the current frame (k) can be obtained by adding the difference between the pre-processed image components to the primary radiation component Pg(k-1) in the preceding frame (k-1).

The primary radiation component Pg(k-1)n calculated in the preceding frame (k-1) is a value converged by the iterative calculation and close to the true value. The convergence of equations (4) and (5) can be accelerated by using this value as the initial value of the current frame (k). Also, the amount of change (the amount of motion) between frames is corrected by the difference between the pre-processed images. This makes it possible to reduce the influence of an error caused by the amount of motion of the object between the frames. Even when there is a motion between frames, therefore, it is possible to accelerate the convergence of equations (4) and (5), reduce the influence of an artifact, and estimate the primary radiation component Pg(k) having a higher contrast and higher image quality, in the same manner as when there is no motion.

The scattered ray estimating unit 104 calculates the primary radiation component Pg(k)n close to the true value by iteratively executing the scattered ray estimating process. The scattered ray estimating unit 104 calculates the scattered ray component S(k) based on equation (1) from the component of the actual pre-processed image M(k) and the primary component Pg(k)n of the radiation, and outputs the calculated scattered ray component S(k) as a scattered ray image.

In step S306, the scattered ray estimating unit 104 stores, in the storage unit 2015, an image (primary radiation image) based on the primary radiation component Pg calculated in step S305, and the pre-processed image M, for the processing of the next and subsequent frames.

In step S307, the scattered ray reducing unit 105 generates an image (scattered ray reduced image) by subtracting a scattered ray component corresponding to the primary radiation component obtained by the scattered ray estimating unit 104 from an image component obtained by pre-processing a frame to be processed. That is, the scattered ray reducing unit 105 generates the scattered ray reduced image by performing, as the scattered ray reducing process, a weighted subtraction process of subtracting the scattered ray component S(k) obtained in step S305 from the pre-processed image (the component of the actual pre-processed image M(k)) by weighted subtraction.

In step S308, the post-processing unit 106 performs post-processing on the scattered ray reduced image, thereby generating a post-processed image.

Then, in step S309, the output control unit 107 outputs the post-processed image having undergone the post-processing in step S308 to the image output unit (the display unit 205 or 209, or the storage unit 206).

In this embodiment, in the scattered ray estimating process which is iteratively executed, the scattered ray estimating unit 104 can perform calculations by using the number of iterations as a fixed value. When the number of iterations is a fixed value, the processing speed remains the same between frames, so it is possible to prevent phenomena such as variations and drop frame when performing monitor display. In order to increase the operation speed, the scattered ray estimating unit 104 can set the number of iterations which is a fixed value to the number of iterations matching the convergence speed of the second and subsequent frames.

By this embodiment, an image having a higher contrast and higher image quality can be obtained by reducing the influence of a scattered ray, even in imaging using no grid. Also, even for a moving image using no grid, an image having a higher contrast and higher image quality can be obtained while maintaining the frame rate of the moving image.

Second Embodiment

In the first embodiment, as an example of the calculation by which the amount of change obtaining unit 103 obtains the amount of change between frames, an example using the difference between the frames from a plurality of pre-processed images has been explained. That is, an example in which the amount of change obtaining unit 103 obtains the amount of change between frames based on the difference between the component of the pre-processed image M(k) of the current frame and the component of the pre-processed image M(k-1) of the preceding frame has been explained.

In this embodiment, as an example of the calculation for obtaining the amount of change between frames, an example in which a value which is one of the differences between the component of a pre-processed image M(k) of the current frame and the components of pre-processed images M(k-1, k-2, ... ) of a plurality of preceding frames and minimizes the squared error of the whole image is used as an estimated value of the amount of change will be explained.

Processes in steps S301 and S302 are the same as the processes in the first embodiment, so an explanation thereof will be omitted. Also, the processing of the first frame of a moving image is the same as that in the first embodiment, so an explanation thereof will be omitted.

In determination of step S303, a CPU (Central Processing Unit) 2012 determines whether a frame to be processed is the first frame of moving image capturing. If the frame to be processed is not the first frame (NO in step S303), the CPU (Central Processing Unit) 2012 advances the process to step S304.

In step S304, an amount of change obtaining unit 103 receives a plurality of pre-processed images, and obtains the amount of change between frames. Of the plurality of pre-processed images, a value which is one of the differences between the component of the pre-processed image M(k) of the current frame and the components of the pre-processed images M(k-1, k-2, ... ) of a plurality of preceding frames and minimizes the squared error of the whole image is used as an obtained value of the amount of change.

The amount of change obtaining unit 103 obtains a preceding frame (preceding frame number kmin) which minimizes a value based on the differences between an image component obtained by pre-processing a frame (k) to be processed, and image components obtained by pre-processing a plurality of preceding frames (k-1, k-2, ..., k-t) of the frame (k). Then, the amount of change obtaining unit 103 sets the difference between the image component (M(k)) obtained by pre-processing the frame to be processed and the image component (M(min)) of the obtained preceding frame, as the amount of change (the amount of motion).

More specifically, the amount of change obtaining unit 103 obtains the differences between the pre-processed image M(k) of the current frame (kth frame) and the pre-processed images M(k-1, k-2, ..., k-t) of the plurality of preceding frames stored in a storage unit 2015, and obtains a value which is one of the obtained differences and minimizes the squared error of the whole image, as an obtained value D(k) of the amount of change as indicated by equation (9):

$$D(k) = M(k) - M(k\ \min) \quad (9)$$

$$k\ \min = MinIndex\left(\sum_{i,j} |M(k,i,j) - M(k-1,i,j)|^2,\right.$$

$$\sum_{i,j} |M(k,i,j) - M(k-2,i,j)|^2, \ldots ,$$

$$\left.\sum_{i,j} |M(k,i,j) - M(k-t,i,j)|^2\right)$$

In equation (9), a function MinIndex indicating kmin is a function of obtaining the differences between the component of the pre-processed image M(k) of the current frame (kth frame) and the components of the pre-processed images M(k-1, k-2, ..., k-t) of the plurality of preceding frames, and selecting the frame number kmin which is one of the obtained differences and minimizes the squared error of the whole image. Also, i and j represent coordinates, and the sum total of values at each coordinate is calculated.

When imaging a periodically moving object, a most similar frame is not a preceding frame but a periodically matching frame in some cases. Therefore, by finding a minimum value of the error as in equation (9) using the pre-processed images M(k-1, k-2, ..., k-t) of the plurality of preceding frames, a primary radiation component most similar to a primary radiation component Pg(k) of the current frame can be set as an initial value from primary radiation components Pg(k-1, k-2, ..., k-t) of a plurality preceding frames.

By thus setting a more similar component as the initial value, even when there is a motion between frames, it is possible to accelerate the convergence of the iterative calculations in equations (4) and (5), estimate the primary radiation component Pg(k) in which the influence of an artifact is reduced, and further reduce the deterioration of the image quality.

By using the estimated value D(k) of the amount of change of equation (9) in equation (7), a value taking account of the estimated value D(k) of the amount of change of equation (9) is set as the initial value (a value when number of iterations n=1) of the primary component Pg(k) of the radiation.

In step S305, a scattered ray estimating unit 104 performs a scattered ray estimating process based on the component of the pre-processed image M(k) of the current frame, the estimated value D(k) of the amount of change, and an image (primary radiation image) based on a primary radiation component Pg(k-1)n of the preceding frame stored in the storage unit 2015, thereby generating a scattered ray image.

The scattered ray estimating unit 104 calculates a primary radiation component Pg(k)n close to the true value by iteratively executing the scattered ray estimating process. The scattered ray estimating unit 104 calculates a scattered ray component S(k) based on equation (1) from the component of the actual pre-processed image M(k) and the primary component Pg(k)n of the radiation, and outputs the calculated scattered ray component S(k) as a scattered ray image.

In step S306, the scattered ray estimating unit 104 stores, in the storage unit 2015, an image (primary radiation image) based on the primary radiation component Pg calculated in step S305 and the pre-processed image M, for the processing of the next and subsequent frames. The storage unit 2015 can store data of a plurality of frames, and this data stored in the storage unit 2015 is referred to in processing in step S304 (estimation of the amount of change) and in step S305 (generation of the scattered ray image).

In step S307, a scattered ray reducing unit 105 performs, as a scattered ray reducing process, a weighted subtraction process of subtracting the scattered ray component S(k) obtained in step S305 from the pre-processed image (the component of the actual pre-processed image M(k)) by weighted subtraction, thereby generating a scattered ray reduced image. In step S308, a post-processing unit 106 performs post-processing on the scattered ray reduced image, thereby generating a post-processed image. Then, in step S309, an output control unit 107 outputs the post-processed image having undergone the post-processing in step S308 to an image output unit (a display unit 205 or 209, or a storage unit 206).

In this embodiment, a primary radiation image most similar to a primary radiation image of the current frame can be set as an initial value by obtaining an estimated value of the amount of change by using information of a plurality of past frames. Even when there is a motion between frames, therefore, it is possible to accelerate the convergence of the iterative calculation, estimate a primary radiation image in which the influence of an artifact is reduced, and further reduce the deterioration of the image quality.

Third Embodiment

In the first embodiment, as an example of the calculation by which the amount of change obtaining unit 103 obtains the amount of change (the amount of motion) between frames, an example using the difference between the frames from a plurality of pre-processed images has been explained. In this embodiment, an arrangement which increases the processing speed by reducing the image size if the amount of change (the amount of motion) exceeds a threshold will be explained.

Figure 5:
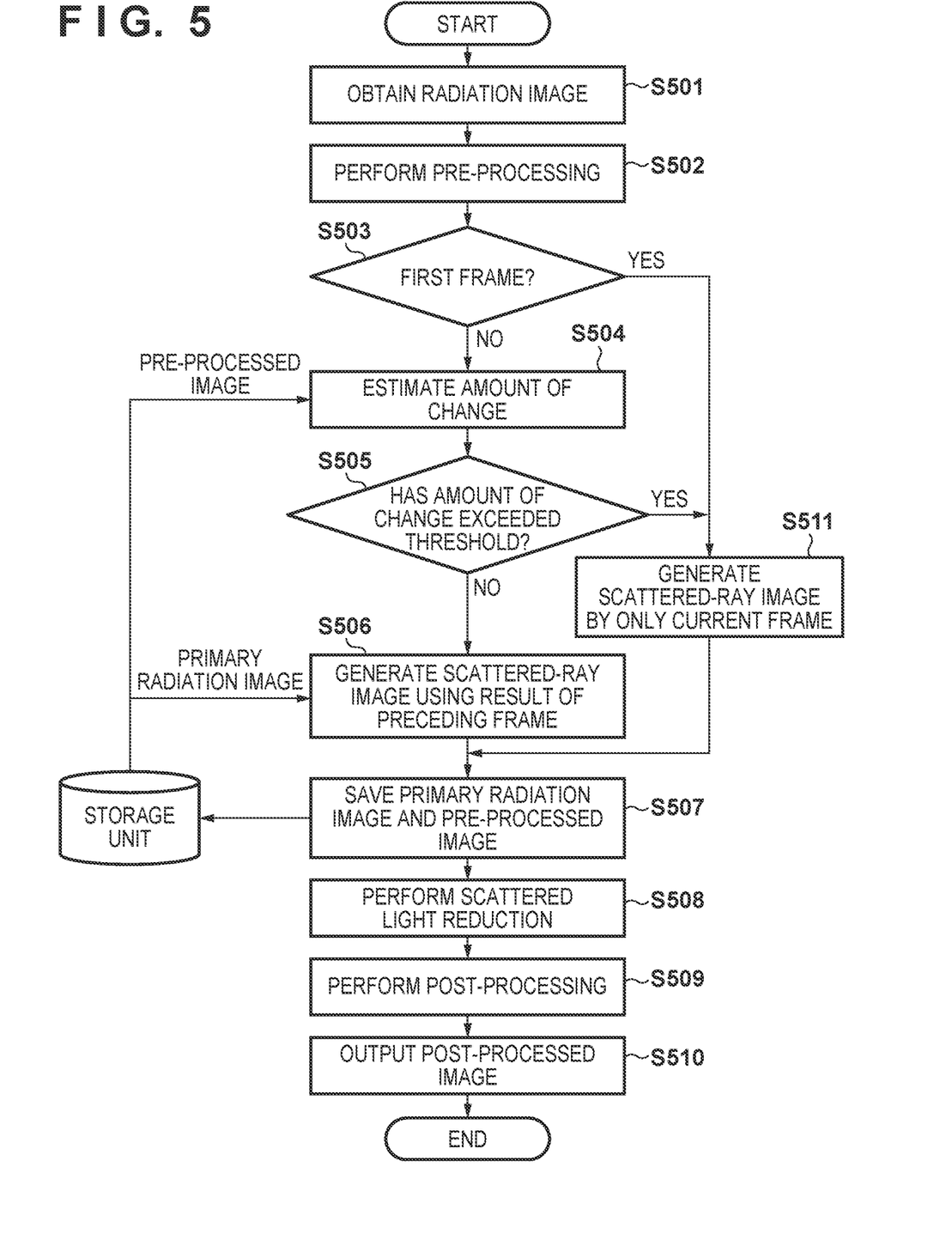
FIG. 5 is a flowchart for explaining the procedure of image processing according to another embodiment.

FIG. 5 is a flowchart for explaining the procedure of image processing according to the third embodiment. First, the processing of the first frame of a moving image will be explained.

(Processing of First Frame of Moving Image)

Processes in steps S501 and S502 are the same as the processes in steps S301 and S302 of the first embodiment, so an explanation thereof will be omitted.

In step S503, a CPU (Central Processing Unit) 2012 determines whether a frame to be processed is the first frame of moving image capturing. If the frame to be processed is not the first frame (NO in step S503), the CPU (Central Processing Unit) 2012 advances the process to step S504. If the frame to be processed is the first frame of moving image capturing (YES in step S503), the CPU (Central Processing Unit) 2012 advances the process to step S511.

In step S511, a scattered ray estimating unit 104 performs a scattered ray estimating process by using only the component of a pre-processed image M(k) of the current frame, thereby generating a scattered ray image. As in the first embodiment, the scattered ray estimating process estimates a primary component Pg(k) of radiation so that an error E of equation (2) decreases.

When executing the scattered ray estimating process, the scattered ray estimating unit 104 performs a reducing process on the pre-processed image M(k) as pre-processing. As this reducing process, the scattered ray estimating unit 104 can use an image reducing technique such as bilinear interpolation, bicubic interpolation, or nearest neighbor interpolation. The estimation time can be shortened by reducing the image. When performing estimation by using the reduced image, the scattered ray estimating unit 104 can estimate the primary component Pg(k) of the radiation by the reduced size by changing the scattered ray kernel for reduction.

The image of a calculated primary radiation component Pg(k)n has the same image size as that of the reduced pre-processed image M(k). After calculating the primary radiation component Pg(k)n, therefore, the scattered ray estimating unit 104 performs an enlarging process so as to obtain the same size as that of the original pre-processed image M(k). The scattered ray estimating unit 104 calculates a scattered ray component S(k) based on equation (1) from the component of the actual pre-processed image M(k) and the primary radiation component Pg(k)n having undergone the enlarging process, and outputs the calculated scattered ray component S(k).

In step S507, the scattered ray estimating unit 104 stores, in a storage unit 2015, an image (primary radiation image) based on the calculated primary radiation component Pg(k)n and the pre-processed image M(k), for the processing of the next and subsequent frames.

Then, in step S508, a scattered ray reducing unit 105 performs a scattered ray reducing process. In step S509, a post-processing unit 106 performs post-processing on the scattered ray reduced image, thereby generating a post-processed image. In step S510, an output control unit 107 outputs the post-processed image having undergone the post-processing in step S509 to an image output unit (a display unit 205 or 209, or a storage unit 206). Processes in steps S508 to S510 are the same as the processes in steps S307 to S309 explained in the first embodiment.

(Processing of Second and Subsequent Frames of Moving Image)

The processing of the second and subsequent frames of the moving image will be explained below. Processes in steps S501 and S502 are the same as the processes for the first frame, so an explanation thereof will be omitted.

Then, in determination in step S503, the CPU (Central Processing Unit) 2012 determines whether a frame to be processed is the first frame of moving image capturing. If the frame to be processed is not the first frame (NO in step S503), the CPU (Central Processing Unit) 2012 advances the process to step S504.

In step S504, an amount of change obtaining unit 103 receives a plurality of pre-processed images, and estimates (obtains) the amount of change between frames. The amount of change between frames is estimated (obtained) based on the difference between a pre-processed image of the current frame and a pre-processed image of the preceding frame, as the plurality of pre-processed images. The amount of change obtaining unit 103 obtains an estimated value D(k) of the amount of change between frames as indicated by equation (6), from the component of the pre-processed image M(k) of the current frame (kth frame), and the component of a pre-processed image M(k-1) of the preceding frame ((k-1)th frame) stored in the storage unit 2015.

Then, the amount of change obtaining unit 103 obtains evaluation information for evaluating the amount of change. As the evaluation information, the amount of change obtaining unit 103 obtains a mean squared error mse(k) by equation (10) below, based on the estimated value of the amount of change obtained from equation (6). In equation (10), i and j represent coordinates, and the amount of change obtaining unit 103 obtains the mean squared error mse(k), as the evaluation information of the amount of change, by dividing the sum total of values at each coordinate by a total number N of pixels.

$$mse(k) = \frac{1}{N} \sum_{i,j} |D(k, i, j)|^2 \qquad (10)$$

In step S505, the amount of change obtaining unit 103 compares the evaluation information of the amount of change with a threshold. Based on the result of this comparison, the scattered ray estimating unit 104 changes the process of estimating the scattered ray component and the primary component of the radiation.

The amount of change obtaining unit 103 compares the evaluation information (mean squared error mse(k)) of the amount of change with a threshold thMse. The threshold thMse is a threshold for determining whether the amount of change is correctable when equation (7) taking account of the estimated value D(k) of the amount of change is used as the initial value.

For a frame in which the evaluation information (mean squared error mse(k)) of the amount of change (the amount of motion) has a value larger than the threshold (thMse) (YES in step S505), it is determined that correction using a result of equation (7) as the initial value is impossible, and the process is advanced to step S511.

In step S511, if the evaluation information of the amount of change (the amount of motion) exceeds the threshold, the scattered ray estimating unit 104 sets the image component (M(k)) obtained by pre-processing the frame (k) to be processed, as the initial value of the iterative calculation of the frame (k) to be processed. In this step, neither the primary radiation component (Pg(k-1)) estimated in the preceding frame (k-1) of the frame (k) nor the image component (M(k-1)) of the preceding frame is used in the setting of the initial value.

That is, the scattered ray estimating unit 104 generates a scattered ray image by performing the scattered ray estimating process by using only the component of the pre-processed image M(k) of the current frame. A method of estimating the scattered ray by using only the pre-processed image of the current frame is the same as the scattered ray estimating process for the first frame. When executing the scattered ray estimating process in this step, the scattered ray estimating unit 104 can perform a reducing process as pre-processing on the frame to be processed.

On the other hand, if it is determined in step S505 that the evaluation information of the amount of change (the amount of motion) is equal to or smaller than the threshold, the scattered ray estimating unit 104 sets a value obtained by combining the primary radiation component (Pg(k-1)) estimated in the preceding frame (k-1) of the frame (k) to be processed and the amount of change (the amount of motion D(k)), as the initial value of the iterative calculation of the frame (k). That is, for a frame in which the evaluation information (mean squared error mse(k)) has a value equal to or smaller than the threshold (thMse) (NO in step S505), the scattered ray estimating unit 104 determines that correction using equation (7) as the initial value is possible, and advances the process to step S506.

In step S506, the scattered ray estimating unit 104 performs the scattered ray estimating process based on the component of the pre-processed image M(k) of the current frame, the estimated value D(k) of the amount of change, and the image (primary radiation image) based on the primary radiation component Pg(k-1)n of the preceding frame stored in the storage unit 2015, thereby generating a scattered ray image. The scattered ray estimating process is the same as the process in the first embodiment.

In step S507, the scattered ray estimating unit 104 stores, in the storage unit 2015, the image (primary radiation image) based on the calculated primary radiation component Pg(k)n and the pre-processed image M(k), for the processing of the next and subsequent frames.

In step S508, the scattered ray reducing unit 105 performs a scattered ray reducing process. In step S509, the post-processing unit 106 performs post-processing on the scattered ray reduced image, thereby generating a post-processed image. In step S510, the output control unit 107 outputs the post-processed image having undergone the post-processing in step S509 to the image output unit (the display unit 205 or 209, or the storage unit 206). The processes in steps S508 to S510 are the same as the processes in steps S307 to S309 explained in the first embodiment.

In this embodiment, the two types of scattered ray estimating methods are switched for the whole frame. However, the scattered ray estimating methods may also be switched for each pixel or each region. The scattered ray estimating unit 104 can switch the settings of the initial value in the scattered ray estimating process for each pixel of a frame in accordance with the amount of change (the amount of motion), and can switch the settings of the initial value in the scattered ray estimating process for each region of a frame in accordance with the amount of change (the amount of motion). Alternatively, the scattered ray estimating unit 104 can switch the settings of the initial value in the scattered ray estimating process in accordance with the presence/absence of an object in a frame.

For example, if correction using equation (7) as the initial value is performed when an object moves in the current frame (k) to a region where there was no object in the preceding frame (k-1), the primary component Pg(k-1)n of the radiation in the preceding frame does not contain the component of the object, and only the component of the estimated value D(k) of the amount of change is the initial value. This may decrease the estimation accuracy of the primary radiation component Pg(k)n in the current frame.

For a region like this, the scattered ray estimating unit 104 performs the scattered ray estimating process by using only the component of the pre-processed image M(k) of the current frame. This process can suppress the decrease in estimation accuracy. After estimating the primary radiation component Pg(k)n by each scattered ray estimating process, the scattered ray estimating unit 104 can also correct pixel values by performing a filtering process on the calculated primary radiation component Pg(k)n, so as not to produce any image unnaturalness between adjacent pixels.

Fourth Embodiment

In the first embodiment, an arrangement which accelerates the convergence of the iterative calculation, reduces the number of iterations, and increases the operation speed by using the value taking account of the estimated value D(k) of the amount of change as an initial value as indicated by equation (7) has been explained. The number of iterations can change in accordance with the closeness of a given initial value to the true value. Since motion correction has its limit, an initial value closer to the true value can be given as the motion becomes smaller.

In this embodiment, as arrangement which changes the number of iterations in accordance with the image capturing condition or the image display condition will be explained. A scattered ray estimating unit 104 can change the number of iterations of the iterative calculation of a primary radiation component based on an imaging condition for a moving image.

For example, the scattered ray estimating unit 104 can change the number of iterations in accordance with the imaging frame rate set as the imaging condition. The higher the frame rate, the smaller the motion of an object, so an initial value closer to the true value can be given. When the frame rate is higher than a threshold frame rate as a reference, the scattered ray estimating unit 104 sets the number of iterations smaller than a preset number of iterations. Of the other hand, when the frame rate is lower than the reference threshold frame rate, the motion between frames becomes larger, so the initial value deviates from the true value. Accordingly, the scattered ray estimating unit 104 sets the number of iterations larger than the preset number of iterations.

The imaging condition is not limited to the imaging frame rate, and the scattered ray estimating unit 104 can change the number of iterations of the iterative calculation of the primary radiation component based on the display condition (display rate) of a moving image in a display unit 205 or 209. For example, when replaying a moving image captured by a high-speed camera at a display rate equal to or lower than the imaging rate, or when performing slow-motion replay, it can take a processing time longer than the imaging time. Therefore, the scattered ray estimating unit 104 can set the number of iterations larger than the preset number of iterations in accordance with the display rate. The scattered ray estimating unit 104 can also change the number of iterations in accordance with the imaged portion of an object or the input image size.

By this embodiment, an image having higher image quality can be obtained by changing the preset number of iterations in accordance with the imaging condition of the image or the display condition of the image.

Fifth Embodiment

In the first embodiment, an arrangement which accelerates the convergence of the iterative calculation, reduces the number of iterations, and increases the operation speed by using the value taking account of the estimated value D(k) of the amount of change as an initial value as indicated by equation (7) has been explained.

If, however, the estimated value D(k) of the amount of change is a large value exceeding the threshold, the average value of the sum of a primary radiation component Pg(k-1)n in the preceding frame and the estimated value D(k) of the amount of change may largely shift from the average value of the initial value of a primary radiation component Pg(k)1 in the current frame.

In this embodiment, an arrangement which, when the estimated value D(k) of the amount of change is a large value exceeding the threshold, adjusts the estimated value of the amount of change by weighting in order to suppress a reduction in convergence speed caused by the deviation of the initial value from the true value will be explained.

If the amount of change (the estimated value D(k) of the amount of change) exceeds the threshold, a scattered ray estimating unit 104 adjusts the amount of change (the estimated value D(k) of the amount of change) by setting a weighted coefficient based on a primary radiation component (Pg(k-1)n) estimated in a preceding frame (k-1) of a frame (k) to be processed, and the component of a pre-processed image M(k-1) in the preceding frame (k-1).

That is, as the initial value (a value when number of iterations n=1) of a primary radiation component Pg(k)1, the scattered ray estimating unit 104 sets a value taking account of the estimated value D(k) of the amount of change as indicated by equation (11):

$$P_g(k)^1 = P_g(k-1)^n + w \cdot D(k) \qquad (11)$$
$$w = \frac{P_g(k-1)^n}{M(k-1)}$$

A weighted coefficient w is a coefficient taking account of the primary radiation component Pg(k-1)n in the preceding frame, and the component of the pre-processed image M(k-1) in the preceding frame.

Note that the scattered ray estimating unit 104 can also adjust the estimated value D(k) of the amount of change by setting different weighted coefficients w based on the estimated value D(k) of the amount of change.

It is possible to suppress the shift of the average value and suppress the reduction in convergence speed by adjusting the estimated value D(k) of the amount of change by the weighted coefficient taking account of the primary radiation component Pg(k-1)n in the preceding frame and the component of the pre-processed image M(k-1).

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2018-015504, filed Jan. 31, 2018, which is hereby incorporated by reference herein in its entirety.

What is claimed is:

1. An image processing apparatus for processing a moving image obtained by irradiating an object with radiation, comprising:
at least one memory storing instructions; and
at least one processor that when executing the instructions, causes the image processing apparatus to function as:
an obtaining unit configured to obtain an amount of change between frames in the moving image;
an estimating unit configured to estimate, based on the amount of change, a scattered ray component of the radiation scattered by the object in a frame of the moving image; and
a scattered ray reducing unit configured to generate an image by subtracting the scattered ray component from the frame of the moving image,
wherein the obtaining unit obtains a difference between a frame to be processed and a preceding frame of the frame, as the amount of change.

2. The apparatus according to claim 1, wherein the estimating unit estimates a primary component of the radiation by an iterative calculation, and
sets, as an initial value of an iterative calculation of a frame to be processed, a value obtained by combining a primary radiation component estimated in a preceding frame of the frame and the amount of change.

3. The apparatus according to claim 2, wherein in the iterative calculation of the primary component of the radiation, the estimating unit estimates a primary component of radiation when the number of iterations is n+1 (n is an integer of not less than 2), based on a result of multiplication of a result of division, which is obtained by dividing an image component of a frame to be processed by a sum of a primary component of the radiation when the number of iterations is n and the scattered ray component, and the primary component of the radiation.

4. The apparatus according to claim 3, wherein in the iterative calculation of the primary component of the radiation, the estimating unit estimates an image component obtained by pre-processing a frame to be processed, based on the estimated primary radiation component and the scattered ray component.

5. The apparatus according to claim 4, wherein in the iterative calculation of the primary component of the radiation,
the estimating unit obtains an image component estimated value which minimizes a value based on a difference between the image component obtained by pre-processing the frame to be processed and the estimated image component, and
obtains a primary component based on the obtained image component estimated value, and a scattered ray component corresponding to the primary component, and
the scattered ray reducing unit generates an image by subtracting the obtained scattered ray component corresponding to the primary component from the image component obtained by pre-processing the frame to be processed.

6. The apparatus according to claim 2, wherein
the obtaining unit compares evaluation information of the amount of change with a threshold, and
the estimating unit changes the process of estimating the scattered ray component and the primary component, based on a result of the comparison.

7. The apparatus according to claim 6, wherein if the evaluation information of the amount of change exceeds the threshold, the estimating unit sets an image component obtained by pre-processing a frame to be processed, as an initial value of an iterative calculation of the frame to be processed.

8. The apparatus according to claim 7, wherein when executing a scattered ray estimating process, the estimating unit performs a reducing process as pre-processing on a frame to be processed.

9. The apparatus according to claim 6, wherein if the evaluation information of the amount of change is not more than the threshold, the estimating unit sets a value obtained by combining the amount of change and a primary component estimated in a preceding frame of a frame to be processed, as an initial value of an iterative calculation of the frame to be processed.

10. The apparatus according to claim 6, wherein the estimating unit switches settings of an initial value in a scattered ray estimating process for each pixel of the frame, in accordance with the amount of change.

11. The apparatus according to claim 10, wherein the estimating unit switches the settings of the initial value in the scattered ray estimating process, in accordance with presence/absence of an object in the frame.

12. The apparatus according to claim 6, wherein the estimating unit switches settings of an initial value in a scattered ray estimating process for each region of the frame, in accordance with the amount of change.

13. The apparatus according to claim 2, wherein the estimating unit changes the number of iterations of the iterative calculation of the primary radiation component based on an imaging condition of the moving image.

14. The apparatus according to claim 2, wherein the estimating unit changes the number of iterations of the iterative calculation of the primary radiation component based on a condition under which the moving image is displayed on a display unit.

15. The apparatus according to claim 1, wherein the obtaining unit obtains a preceding frame which minimizes a value based on differences between an image component obtained by pre-processing the frame to be processed, and image components obtained by pre-processing a plurality of preceding frames of the frame.

16. The apparatus according to claim 15, wherein the obtaining unit sets a difference between the image component obtained by pre-processing the frame to be processed, and an image component of an obtained preceding frame, as the amount of change.

17. The apparatus according to claim 1, wherein if the amount of change exceeds a threshold, the estimating unit adjusts the amount of change by setting a weighted coefficient based on a primary radiation component estimated in a preceding frame of a frame to be processed, and an image component of the preceding frame.

18. An image processing apparatus for processing a moving image obtained by irradiating an object with radiation, comprising:

at least one memory storing instructions; and at least one processor that when executing the instructions, causes the image processing apparatus to function as:

an obtaining unit configured to obtain an amount of motion based on a motion of the object or a sensor in the moving image;

an estimating unit configured to estimate, based on the amount of motion, a scattered ray component of the radiation scattered by the object in a frame of the moving image; and a scattered ray reducing unit configured to generate an image by subtracting the scattered ray component from a frame of the moving image, wherein the obtaining unit obtains a difference between a frame to be processed and a preceding frame of the frame, as the amount of motion.

19. A radiation imaging apparatus for processing a moving image obtained by irradiating an object with radiation, comprising:

at least one memory storing instructions; and at least one processor that when executing the instructions, causes the radiation imaging apparatus to function as:

an obtaining unit configured to obtain an amount of change between frames in the moving image;

an estimating unit configured to estimate, based on the amount of change, a scattered ray component of the radiation scattered by the object in a frame of the moving image; and a scattered ray reducing unit configured to generate an image by subtracting the scattered ray component from the frame of the moving image, wherein the obtaining unit obtains a difference between a frame to be processed and a preceding frame of the frame, as the amount of change.

20. An image processing method of processing a moving image obtained by irradiating an object with radiation, comprising:

obtaining a difference between a frame to be processed and a preceding frame of the frame, as an amount of change between frames in the moving image;

estimating, based on the amount of change, a scattered ray component of the radiation scattered by the object in a frame of the moving image; and generating an image by subtracting the scattered ray component from the frame of the moving image.

21. A non-transitory computer-readable storage medium storing a program for causing a computer to execute an image processing method of processing a moving image obtained by irradiating an object with radiation, the image processing method comprising:

obtaining a difference between a frame to be processed and a preceding frame of the frame, as an amount of change between frames in the moving image;

estimating, based on the amount of change, a scattered ray component of the radiation scattered by the object in a frame of the moving image; and generating an image by subtracting the scattered ray component from the frame of the moving image.

* * * * *